United States Patent [19]

Suzuki et al.

[11] Patent Number: 5,700,396
[45] Date of Patent: Dec. 23, 1997

[54] COSMETIC COMPOSITIONS AND AN EMULSION COMPOSITION

[75] Inventors: Masao Suzuki, Nara-ken; Koichi Saito, Amagasaki; Masahide Nakata, Nishinomiya, all of Japan

[73] Assignee: NOF Corporation, Tokyo, Japan

[21] Appl. No.: 734,014

[22] Filed: Oct. 18, 1996

Related U.S. Application Data

[62] Division of Ser. No. 66,017, filed as PCT/JP92/01229, Sep. 25, 1992, Pat. No. 5,589,515.

[30] Foreign Application Priority Data

Sep. 27, 1991 [JP] Japan ................. 3-276697
Dec. 11, 1991 [JP] Japan ................. 3-351403

[51] Int. Cl.$^6$ ............... B01J 13/00; A61K 7/00; A61K 31/185
[52] U.S. Cl. ............... 252/309; 252/311; 252/312; 424/63; 424/400; 424/401; 512/1; 514/456; 514/458; 514/784; 514/785; 514/844; 514/845; 514/937; 514/938; 514/944; 514/945
[58] Field of Search ............... 252/309, 311, 252/312; 424/63, 400, 401; 512/1; 514/456, 458, 784, 785, 844, 845, 937, 938, 944, 945

[56] References Cited

U.S. PATENT DOCUMENTS

| | | |
|---|---|---|
| 4,393,043 | 7/1983 | Koubanis et al. ................. 424/59 |
| 4,601,856 | 7/1986 | Suzuki et al. . |
| 4,740,432 | 4/1988 | Bosserelle ................. 424/59 |
| 5,589,515 | 12/1996 | Susuki et al. ................. 514/784 |

FOREIGN PATENT DOCUMENTS 225946  12/1985  European Pat. Off. .

OTHER PUBLICATIONS

Cosmetic & Toiletries, Mar. 1984, vol. 99, pp. 66, 70–72 and 68.
Abstract of JP 3-115,208 May 16, 1991.
Abstract of JP 63-126543 May 30, 1988.

*Primary Examiner*—Shelley A. Dodson
*Attorney, Agent, or Firm*—Millen, White, Zelano, & Branigan, P.C.

[57] ABSTRACT

A cosmetic composition and an emulsion composition respectively comprising 0.1 to 99 weight % of an oily component and 99.9 to 1 weight % of a watery component are are provided and the oily component in the compositions comprises 85 or more weight % of cis-Δ9-octadecenoic acid or derivatives thereof and contains 90 weight % or more of a cis-Δ9-alkenoic acid or derivatives thereof and 10 weight % or less of fatty acids other than the cis-Δ9-alkenoic acid, derivatives thereof or other oily components. The cosmetic composition showing superior feeling in use and superior storage stability than conventional products and the emulsion composition showing superior stability of emulsion than conventional products can be provided because the oily component contains cis-Δ9-octadecenoic acid or derivatives thereof in a high concentration.

12 Claims, No Drawings

COSMETIC COMPOSITIONS AND AN EMULSION COMPOSITION

This application is a divisional of Ser. No. 08/066,017, filed May 27, 1993, now U.S. Pat. No. 5,589,515 which is a 35 U.S.C. §371 application of International Application Ser. No. PCT/JP92/01229, filed Sep. 25, 1992.

TECHNICAL FIELD

The present invention relates to a cosmetic composition and an emulsion composition comprising cis-Δ9-octadecenoic acid or derivatives thereof in the oily component in a high concentration.

BACKGROUND ART

A cosmetic composition containing cis-Δ9-octadecenoic acid (oleic acid) or derivatives thereof in a high concentration has not been known heretofore.

Conventional oleic acids and derivatives thereof have a bad smell, are colored, cause skin irritation, have a poor feel in use and have poor storage stability tending to further increase the poor smell and color described above.

A method of production of a high purity oleic acid was disclosed in Japanese Patent Application Laid Open No. 1986-297 (Japanese Patent Publication No. 1990-57120). The following methods of production of derivatives of the high purity oleic acid were also disclosed: a method of production of glycerol monooleate in Japanese Patent Application Laid Open No. 1987-132841, a method of production of propylene glycol monooleate in Japanese Patent Application Laid Open No. 1987-138451, a method of production of polyalkylene glycol monooleate in Japanese Patent Application Laid Open No. 1987-138452, a method of production of sorbitan monooleate in Japanese Patent Application Laid Open No. 1987-142141, a method of production of polyalkylene glycol alkyl ether oleate in Japanese Patent Application Laid Open No. 1987-153250, a method of production of polyoxyalkylene polyalcohol oleate in Japanese Patent Application Laid Open No. 1987-153251, a method of production of polyoxyalkylene polyalcohol oleate in Japanese Patent Application Laid Open No. 1987-153252, a method of production of oleic esters in Japanese Patent Application Laid Open No. 1987-153253, a method of production of polyalkylene glycol oleate in Japanese Patent Application Laid Open No. 1987-153254, a method of production of polyoxyalkylene glycol monooleate in Japanese Patent Application Laid Open No. 1987-153255 and a method of production of polyglycerol oleate in Japanese Patent Application Laid Open No. 1987-153256. It has been suggested that these high purity oleic acids and derivatives thereof have no color, no smell, are stable, cause little skin irritation and can be utilized in the field of pharmaceuticals, cosmetics, foods, synthetic resins, lubricants, biochemicals and the like. However no description can be found on specific cosmetic compositions.

The present invention has the object to provide a cosmetic composition and an emulsion composition both comprising cis-Δ9-octadecenoic acid or derivatives thereof in a high concentration and to provide a cosmetic composition having superior feeling in use and superior storage stability than conventional products and an emulsion composition showing superior emulsion stability than conventional products.

DISCLOSURE OF THE INVENTION

The present invention provides a cosmetic composition which comprises 0.1 to 99 weight % of an oily component and 99.9 to 1 weight % of a watery component, the oily component comprising 85 or more weight % of cis-Δ9-octadecenoic acid or derivatives thereof and containing 90 weight % or more of a cis-Δ9-alkenoic acid or derivatives thereof and 10 weight % or less of fatty acids other than the cis-Δ9-alkenoic acid, derivatives thereof or other oily components.

The present invention also provides an emulsion composition which comprises 0.1 to 99 weight % of an oily component and 99.9 to 1 weight % of a watery component, the oily component, comprising 85 or more weight % of cis-Δ9-octadecenoic acid or derivatives thereof, containing 90 weight % or more of a cis-Δ9-alkenoic acid or derivatives thereof and 10 weight % or less of fatty acids other than the cis-Δ9alkenoic acid, derivatives thereof or other oily components and having an oily substance insoluble in the watery component and a surfactant which is dissolved or emulsified in the watery component.

THE MOST PREFERRED EMBODIMENT TO CARRY OUT THE INVENTION

The invention is described in more detail in the following.

The ratio of the oily component and the watery component is 0.1 to 99 weight %: 99.9 to 1 weight %. However, this ratio is adopted for general cosmetic compositions and the ratio is different depending on the kind of the cosmetic composition. For example, the following ratios can be adopted: for skin lotion, 0.5 to 20 weight %: 99.5 to 80 weight %; for skin cream, 10 to 85 weight %: 90 to 15 weight %; for milk lotion, 3 to 50 weight %: 97 to 50 weight %; and for cleansing foam, 30 to 70 weight %: 70 to 30 weight %.

The cis-Δ9-alkenoic acid in the invention is a fatty acid having one cis-unsaturated bond at the 9-position, such as cis-Δ9-octadecenoic acid (generally called oleic acid), cis-Δ9-hexadecenoic acid (generally called palmitoleic acid) and the like.

The derivatives of the cis-Δ9-alkenoic acid (including cis-Δ9-octadecenoic acid) comprise the following derivatives:

(1) Salts: salts of alkali metals, such as sodium, potassium and the like; ammonium salts; morpholine salts; salts of alkylamines, such as methylamine, ethylamine, butylamine and the like; salts of alkanolamines, such as monoethanolamine, diethanolamine, triethanolamine, triisopropanolamine, 2-amino-2-methyl-1-propanol, 2-amino-2-methyl-1,3-propanediol; salts of basic amino acids, such as arginine and the like; and the like salts;

(2) Amides (these amides are cis-Δ9-alkenoic acid amides): amides with alkylamines or alkenylamines, such as methylamine, ethylamine, butylamine, cis-Δ9-alkenyl amines and the like; amides with alkanolamines, such as monoethanolamine, diethanolamine, isopropanolamine, 2-amino-2-methyl-1-propanol, 2-amino-2-methyl-1,3-propanediol and the like; polyoxyethylated compounds and polyoxypropylated compounds of these amides; amides and salts of amides of amino acids, such as glutamic acid and the like; amides with sodium N-methyltaurine; cis-Δ9-alkenoyl peptides, such as cis-Δ9-alkenoyl collagen and the like; and the like amides;

(3) Esters: esters with monohydric alcohols, such as methanol, ethanol, propanol, isopropanol, butanol, neopentanol, hexanol, octanol, 2-ethylhexanol, nonanol, isononanol, decanol, dodecanol, isotridecanol, tetradecanol, hexadecanol, isohexadecanol, hexyldecanol, octadecanol, isooctadecanol, eicosanol, 2-octyldodecanol, docosanol, octacosanol, triacontanol, aryl alcohol, hexadecenol, cis-Δ9-octadecenol, decocenol, cyclohexanol, lanolin alcohol, terpene alcohol, benzyl alcohol and the like, and esters with polyoxyethylated compounds or polyoxypropylated compounds of the monohydric alcohols; esters with polyhydric alcohols, such as ethylene glycol, propylene glycol, butylene glycol, glycerol, polyglycerols, trimethylolpropane, pentaerythritol, sorbitol, mannitol, sorbitan and the like, and esters with polyoxyethylated compounds or polyoxypropylated compounds of the polyhydric alcohols; esters with sugars, such as glucose, sucrose and the like; esters with sterols, such as cholesterol, cholestanol, sitosterol and the like; esters and salts with other hydroxyl compounds, such as tocopherol, oryzanol, guaiacol, gossypol, terpene alcohols, fluoroalcohols, isethionic acid and the like; phospholipids in which the acyl group of a cis-Δ9-alkenoic acid is introduced; and the like esters;

(4) Derivatives of cis-Δ9-alkenols: cis-Δ9-alkenols derived from cis-Δ9-alkenoic acids; phosphoric esters, sulfuric esters, polyoxyethylated compounds, polyoxypropylated compounds, polyoxyethylated phosphoric esters, polyoxyethylated sulfuric esters, polyoxypropylated phosphoric esters and polyoxypropylated sulfuric esters of the cis-Δ9-alkenols and salts of these compounds; esters, partial esters and partial ester salts of cis-Δ9-alkenyl alcohols with saturated, unsaturated, straight chain, branched chain, monovalent or polyvalent carboxylic acids or hydroxylated carboxylic acids derived from these carboxylic acid, such as ethanoic acid, butanoic acid, 2-ethylhexanoic acid, dodecanoic acid, octadecanoic acid, cis-Δ9-octadecenoic acid, succinic acid, adipic acid, sebacic acid, maleic acid, oxalic acid, citric acid, malic acid and the like; ethers of cis-Δ9-alkenols with alcohols, sugars or hydroxyl compounds described in (3) in the above; and the like compounds; and (5) Derivatives of cis-Δ9-alkenylamines: salts of cis-Δ9-alkenylamines derived from cis-Δ9-alkenoic acids with acids, such as hydrochloric acid, sulfuric acid, nitric acid, phosphoric acid, ethanoic acid and the like; quaternary ammonium salts having a cis-Δ9-alkenyl group; quaternary ammonium betaine having a cis-Δ9-alkenyl group; and the like compounds.

As shown in the above, the derivatives of cis-Δ9-alkenoic acid of the oily component of the invention is an oily substance insoluble in the watery component or a surfactant which is dissolved or emulsified in the watery component. Therefore, the cosmetic composition of the invention includes a composition having two separated layers composed of the oily substance and the watery component, a homogeneous composition composed of the surfactant and the watery component and a homogeneous transparent or turbid composition having the oily substance dissolved, emulsified or dispersed in the watery component by the effect of the surface active agent.

Preferable examples of the derivatives of the cis-Δ9-alkenoic acids as the oily substance are esters of cis-Δ9-octadecenoic acid with ethanol, isopropanol, cis-Δ9-hexadecenol, cis-Δ9-octadecenol, isooctadecanol, cholesterol and tocopherol; glycerol tri-cis-Δ9-octadecenoate; cis-Δ9-octadecenoic acid; cis-Δ9-octadecenol and the like. Preferable examples of the derivatives of the cis-Δ9-alkenoic acids as the surfactant are monoesters of cis-Δ9-octadecenoic acid and glycerol or polyglycerol, sorbitan mono- or sesqui-cis-Δ9-octadecenoate, polyoxyethylated sorbitan mono-cis-Δ9-octadecenoate, polyoxyethylated sorbitol tri- or tetra-cis-Δ9octadecenoate, polyoxyethylene glycol mono-cis-Δ9-octadecenoate and polyoxyethylated cis-Δ9-octadecenyl ether. The particularly preferable examples for both of the oily-substance and the surfactant are esters of cis-Δ9-octadecenoic acid.

In the invention, cis-Δ9-alkenoic acid and the derivative thereof which are the oily component insoluble in the watery component can be solubilized or emulsified in the watery component much more easily by using the surfactant of the derivatives of cis-Δ9-alkenoic acid in comparison to using other surface active agents and the stability is much more excellent. The weight ratio of the oily substance and the surfactant in this case is varied depending on the kinds and the ratio of the oily component and the surfactant, other additives and the like. The ratio is generally in the range of 99 to 1:1 to 99 and preferably in the range of 97 to 3:3 to 97.

The oily component other than those described above are all kinds of oily components other than the cis-Δ9-alkenoic acids and the derivatives thereof. Examples are natural and synthetic oily substances, such as fatty acids and derivatives thereof other than the cis-Δ9-alkenoic acids, paraffin, kerosene, squalane, plant oils, animal oils, lanoline, haze wax, hexadecanol, isooctadecanol, silicone oils, fluorohydrocarbons, polyoxypropylated ethers, cholesterol, tocopherol and the like; surface active agents derived from fatty acids other than the cis-Δ9alkenoic acids, such as dodecandiethanolamide and the like; other surface active agents like polyoxyethylated alkylphenyl ether; and the like.

The watery component functions as the moisturizing agent and the examples include water, of course, and compounds which can be mixed with water in any ratio, such as alcohols like ethanol, isopropanol, ethylene glycol, propylene glycol, 1,3-butylene glycol, polyethylene glycols, glycerol, sorbitol, polyglycerols, polyvinyl alcohols and the like; sugars like glucose, sucrose and the like; mucopolysaccharides like hyaluronic acid and the like; amino acids like glutamic acid and the like; proteins like collagen and the like; and the like compounds.

When other cis-Δ9-alkenoic acids such as palmitoleic acid are present together with cis-Δ9-octadecenoic acid, the other cis-Δ9-alkenoic acids exhibit the same effect as that of cis-Δ9-octadecenoic acid. The oily component contains 85 weight % or more of cis-Δ9-octadecenoic acid and 90 weight % or more of the cis-Δ9-alkenoic acid, preferably 90 weight % or more of cis-Δ9-octadecenoic acid and 93 weight % or more of the cis-Δ9-alkenoic acid, more preferably 95 weight % or more of cis-Δ9octadecenoic acid and 97 weight % or more of the cis-Δ9-alkenoic acid and most preferably 97 weight % or more of cis-Δ9-octadecenoic acid and 99 weight % or more of the cis-Δ9-alkenoic acid. When the content of cis- Δ9-octadecenoic acid is less than 85 weight % or the content of the cis-Δ9alkenoic acid is less than 90 weight %, the feeling in use of the cosmetic composition is not satisfactory.

The cosmetic composition of the invention may comprise components generally added to cosmetic compositions, such as drugs like vitamins, antibiotics and the like, nutrients, ultraviolet ray absorbents, carbon black, titanium oxide, iron oxide, metallic soaps, calcium carbonate, silica, talc, colors, perfumes and the like, in addition to the oily component and the watery component described above.

The cosmetic composition of the invention takes the form of liquid, cream, gel or solid depending on the mixed composition. It is used as skin lotion, cosmetic oil, milk lotion, lipstick, hair liquid, hair cream, hair growth agent, foundation, various kinds of cream and the like.

The emulsion composition of the invention may comprise various kinds of additives generally added to emulsion compositions.

The method of preparation of the cosmetic composition and the emulsion composition of the invention can be performed by compounding the components described above. The order of the addition of the components is not particularly limited and components can be suitably selected and added. The compounded components are suitably mixed by using various kinds of mixer, various kinds of dispersing machine, various kinds of emulsifying machine or the like to prepare the cosmetic composition and the emulsion composition of the invention.

The reason that the stability of the product in the invention is very excellent when the derivative of cis-Δ9-octadecenoic acid is used as the surfactant to emulsify or solubilize in the watery component cis-Δ9-octadecenoic acid or the derivative which is insoluble in the watery component can be considered as following: when the concentration of cis-Δ9-octadecenoic acid or the derivative is high, mutual orientation and cohesion of the cis-Δ9-octadecenoyl group or the cis-Δ9-octadecenyl group in the molecule is considered to be enhanced and the molecular structure proper to the molecule is efficiently exhibited; this is considered to have the effect on the better feeling in use of the cosmetic composition comprising cis-Δ9-octadecenoic acid or the derivative in a high concentration.

The cosmetic composition of the invention comprising cis-Δ9-octadecenoic acid or the derivatives thereof in the oily component in a high concentration provides very excellent feeling in use and the result is remarkably superior than the cosmetic compositions comprising cis-Δ9-octadecenoic acid or the derivatives thereof in a low concentration.

Cosmetic compositions prepared by using commercial oleic acid or derivatives thereof having low concentrations of cis-Δ9-octadecenoic acid as the material are colored or generate smell with passage of time. The cosmetic composition of the invention does not have such drawback.

The emulsion composition of the invention comprising cis-Δ9-octadecenoic acid or the derivative thereof in the oily component in a high concentration has a very excellent stability of the emulsion.

EXAMPLE

The invention is described with reference to examples. However, the invention is by no means limited by the examples.

In the Examples and Comparative Examples, oleic acid or oleic acid derivatives containing various kinds of cis-Δ9-octadecenoic acid and derivatives thereof were used as the oily component. The concentration was represented by the purity of cis-Δ9-octadecenoic acid or a cis-Δ9-alkenoic acid in the oleic acid.

When the concentration of cis-Δ9-octadecenoic acid or its derivative is varied in a composition using two or more kinds of oleic acid or oleic acid derivatives, the oleic acids or the oleic acid derivatives having the same purity of the cis-Δ9-octadecenoic acid were used for compounding in the composition.

In the Examples and Comparative Examples, "%" means "weight %". The oleic acid or the oleic acid derivative containing 57% of cis-Δ9-octadecenoic acid and 66 weight % of cis-Δ9-alkenoic acid used in Comparative Examples is a commercial oleic acid or a derivative from the commercial oleic acid.

Method of evaluation of the cosmetic composition, method of evaluation of storage stability of an emulsion composition and method of analysis of purity of a cis-Δ9-alkenoic acid containing cis-Δ9-octadecenoic acid are described in the following.

Method of evaluation of the feeling in use

Overall feeling in use including all of smell, extension, refreshing feeling and emollient effect was evaluated by 20 women panellers and the result is shown by the number of the panellers whose answer was good.

Method of evaluation of storage stability of an emulsion composition

An oily component (including oily substances and surfactants) and a watery component were mixed by shaking mildly and then emulsified by using a homogenizer (DX-3 type, a product of Nippon Seiki Seisakusho Co., Ltd.) at 10,000 rpm for 15 minutes. Condition of the emulsion was evaluated by visual observation according to the following criterion:

stable: emulsified in a stable condition slightly separated: slightly separated separated: completely separated into two phases Method of analysis of purity Analysis was conducted by using an apparatus for gas chromatography (GC-9A, a product of Shimazu Seisakusho Co., Ltd.) equipped with capillary columns which can separate isomers having different positions of a double bond and different steric structures (SP-2560:0.25 mm×100 m, a product of Supelco Inc.).

Examples 1 to 5 and Comparative Examples 1 to 3

Skin lotions were prepared by using N-oleoyl-L-glutamic acids which are oleic acid derivatives having different purities shown in Table 1 as the surfactant according to the formulation described below and the feeling in use was evaluated. The results are shown in Table 1.

| Formulation | |
| --- | --- |
| oily component | |
| surfactant: N-oleoyl-L-glutamic acid | 3% |
| watery components | |
| ethanol | 10% |
| purified water | 85% |
| sorbitol | 2% |

TABLE 1

| | purity of cis-Δ9-octadecenoic acid (%) | purity of cis-Δ9-alkenoic acid (%) | evaluation of feeling in use (number of persons) |
| --- | --- | --- | --- |
| Example 1 | 99.9 | 100 | 19 |
| Example 2 | 99 | 99.5 | 17 |
| Example 3 | 95 | 97 | 15 |
| Example 4 | 90 | 93 | 15 |
| Example 5 | 85 | 90 | 13 |
| Comparative Example 1 | 80 | 86 | 7 |
| Comparative Example 2 | 70 | 78 | 1 |
| Comparative Example 3 | 57 | 66 | 0 |

Examples 6 to 10 and Comparative Examples 4 to 6

Cleansing creams were prepared by using monosodium N-oleoylglutamates which are oleic acid derivatives having different purities shown in Table 2 as the surfactant according to the formulation described below and the feeling in use was evaluated. The results are shown in Table 2.

| Formulation | |
|---|---|
| oily component | |
| surfactant: monosodium N-oleoylglutamate | 45% |
| watery components | |
| purified water | 50% |
| polyethylene glycol | 5% |

TABLE 2

| | purity of cis-Δ9-octadecenoic acid (%) | purity of cis-Δ9-alkenoic acid (%) | evaluation of feeling in use (number of persons) |
|---|---|---|---|
| Example 6 | 99.9 | 100 | 20 |
| Example 7 | 99 | 99.5 | 18 |
| Example 8 | 95 | 97 | 16 |
| Example 9 | 90 | 93 | 15 |
| Example 10 | 85 | 90 | 13 |
| Comparative Example 4 | 80 | 86 | 10 |
| Comparative Example 5 | 70 | 78 | 7 |
| Comparative Example 6 | 57 | 66 | 0 |

Examples 11 to 15 and Comparative Examples 7 to 9

Skin lotions were prepared by using glycerol monooleates which are oleic acid derivatives having different purities shown in Table 3 and polyoxyethylated (25 mols) oleyl ethers which are oleic acid derivatives having the same purities as those of the corresponding glycerol monooleates as the surfactants according to the formulation described below and the feeling in use was evaluated. The results are shown in Table 3.

| Formulation | |
|---|---|
| oily component | |
| surfactants: glycerol monooleate | 3% |
| polyoxyethylated (25 mols) oleyl ether | 2% |
| watery components | |
| ethanol | 10% |
| purified water | 82% |
| sorbitol | 3% |

TABLE 3

| | purity of cis-Δ9-octadecenoic acid (%) | purity of cis-Δ9-alkenoic acid (%) | evaluation of feeling in use (number of persons) |
|---|---|---|---|
| Example 11 | 99.9 | 100 | 20 |
| Example 12 | 99 | 99.5 | 19 |
| Example 13 | 95 | 97 | 18 |
| Example 14 | 90 | 93 | 18 |
| Example 15 | 85 | 90 | 15 |
| Comparative | 80 | 86 | 9 |

TABLE 3-continued

| | purity of cis-Δ9-octadecenoic acid (%) | purity of cis-Δ9-alkenoic acid (%) | evaluation of feeling in use (number of persons) |
|---|---|---|---|
| Example 7 | | | |
| Comparative Example 8 | 70 | 78 | 0 |
| Comparative Example 9 | 57 | 66 | 0 |

Examples 16 to 20 and Comparative Examples 10 to 12

Skin lotions were prepared by using L-α-dioleoyl phosphatidyl cholines which are oleic acid derivatives having different purities shown in Table 4 and polyoxyethylated (20 mols) sorbitan monooleates which are oleic acid derivatives having the same purities as those of the corresponding L-α-dioleoyl phosphatidyl cholines as the surfactants according to the formulation described below and the feeling in use was evaluated. The results are shown in Table 4.

| Formulation | |
|---|---|
| oily component | |
| surfactants: L-α-dioleoyl phosphatidyl choline | 2% |
| polyoxyethylated (20 mols) sorbitan monooleate | 1% |
| watery components | |
| ethanol | 15% |
| purified water | 80% |
| propylene glycol | 2% |

TABLE 4

| | purity of cis-Δ9-octadecenoic acid (%) | purity of cis-Δ9-alkenoic acid (%) | evaluation of feeling in use (number of persons) |
|---|---|---|---|
| Example 16 | 99.9 | 100 | 20 |
| Example 17 | 99 | 99.5 | 20 |
| Example 18 | 95 | 97 | 18 |
| Example 19 | 90 | 93 | 15 |
| Example 20 | 85 | 90 | 13 |
| Comparative Example 10 | 80 | 86 | 8 |
| Comparative Example 11 | 70 | 78 | 0 |
| Comparative Example 12 | 57 | 66 | 0 |

Examples 21 to 25 and Comparative Examples 13 to 15

Skin lotions were prepared by using N-oleoyl-L-glutamic acids which are oleic acid derivatives having different purities shown in Table 5 and hexaglycerol monooleates which are oleic acid derivatives having the same purities as those of the corresponding N-oleoyl-L-glutamic acids as the surfactants according to the formulation described below and the feeling in use was evaluated. The results are shown in Table 5.

| Formulation | |
|---|---|
| oily component | |
| surfactants: N-oleoyl-L-glutamic acid | 2% |
| hexaglycerol monooleate | 3% |
| watery components | |
| ethanol | 10% |
| purified water | 85% |

TABLE 5

| | purity of cis-Δ9-octadecenoic acid (%) | purity of cis-Δ9-alkenoic acid (%) | evaluation of feeling in use (number of persons) |
|---|---|---|---|
| Example 21 | 99.9 | 100 | 20 |
| Example 22 | 99 | 99.5 | 19 |
| Example 23 | 95 | 97 | 16 |
| Example 24 | 90 | 93 | 14 |
| Example 25 | 85 | 90 | 11 |
| Comparative Example 13 | 80 | 86 | 3 |
| Comparative Example 14 | 70 | 78 | 0 |
| Comparative Example 15 | 57 | 66 | 0 |

Examples 26 to 30 and Comparative Examples 16 to 18

Shaking lotions separated to two phases were prepared by using isooctadecanyl oleates which are oleic acid derivatives having different purities shown in Table 6 as the oily substance and polyoxyethylated (20 mols) sorbitan tetraoleates which are oleic acid derivatives having the same purities as those of the corresponding isooctadecanyl oleates as the surfactant according to the formulation described below and the feeling in use was evaluated. The results are shown in Table 6.

| Formulation | |
|---|---|
| oily components | |
| oily substance: isooctadecanyl oleate | 8% |
| surfactant: polyoxyethylated (20 mols) sorbitan tetraoleate | 0.2% |
| watery components | |
| purified water | 79.8% |
| ethanol | 10% |
| sorbitol | 1% |
| glycerol | 1% |

TABLE 6

| | purity of cis-Δ9-octadecenoic acid (%) | purity of cis-Δ9-alkenoic acid (%) | evaluation of feeling in use (number of persons) |
|---|---|---|---|
| Example 26 | 99.9 | 100 | 20 |
| Example 27 | 99 | 99.5 | 20 |
| Example 28 | 95 | 97 | 18 |
| Example 29 | 90 | 93 | 17 |
| Example 30 | 85 | 90 | 13 |

TABLE 6-continued

| | purity of cis-Δ9-octadecenoic acid (%) | purity of cis-Δ9-alkenoic acid (%) | evaluation of feeling in use (number of persons) |
|---|---|---|---|
| Comparative Example 16 | 80 | 86 | 4 |
| Comparative Example 17 | 70 | 78 | 0 |
| Comparative Example 18 | 57 | 66 | 0 |

Examples 31 to 35 and Comparative Examples 19 to 21

Skin creams were prepared by using hexadecenyl oleates which are oleic acid derivatives having different purities shown in Table 7 as the oily substance and polyoxyethylated (10 mols) oleyl ethers which are oleic acid derivatives having the same purities as those of the corresponding hexadecenyl oleates as the surfactant according to the formulation described below and the feeling in use was evaluated. The results are shown in Table 7.

| Formulation | |
|---|---|
| oily components | |
| oily substance: hexadecenyl oleate | 70% |
| surfactant: polyoxyethylated (10 mols) oleyl ether | 5% |
| watery components | |
| purified water | 22% |
| glycerol | 3% |

TABLE 7

| | purity of cis-Δ9-octadecenoic acid (%) | purity of cis-Δ9-alkenoic acid (%) | evaluation of feeling in use (number of persons) |
|---|---|---|---|
| Example 31 | 99.9 | 100 | 20 |
| Example 32 | 99 | 99.5 | 20 |
| Example 33 | 95 | 97 | 19 |
| Example 34 | 90 | 93 | 18 |
| Example 35 | 85 | 90 | 13 |
| Comparative Example 19 | 80 | 86 | 7 |
| Comparative Example 20 | 70 | 78 | 0 |
| Comparative Example 21 | 57 | 66 | 0 |

Examples 36 to 40 and Comparative Examples 12 to 24

Skin creams were prepared by using ethyl oleates which are oleic acid derivatives having different purities shown in Table 8 as the oily substance and diglycerol monooleates which are oleic acid derivatives having the same purities as those of the corresponding ethyl oleates as the surfactant according to the formulation described below and the feeling in use was evaluated. The results are shown in Table 8.

| Formulation | |
|---|---|
| oily components | |
| oily substance: ethyl oleate | 65% |
| surfactant: diglycerol monooleate | 5% |
| watery component | |
| purified water | 30% |

TABLE 8

| | purity of cis-Δ9-octadecenoic acid (%) | purity of cis-Δ9-alkenoic acid (%) | evaluation of feeling in use (number of persons) |
|---|---|---|---|
| Example 36 | 99.9 | 100 | 20 |
| Example 37 | 99 | 99.5 | 20 |
| Example 38 | 95 | 97 | 18 |
| Example 39 | 90 | 93 | 18 |
| Example 40 | 85 | 90 | 14 |
| Comparative Example 22 | 80 | 86 | 7 |
| Comparative Example 23 | 70 | 78 | 1 |
| Comparative Example 24 | 57 | 66 | 0 |

Examples 41 to 45 and Comparative Examples 25 to 27

Oleyl oleates of different purities were prepared by esterification of oleic acids having different purities shown in Table 9 with oleyl alcohols having the same purities as those of the corresponding oleic acids which were prepared by reduction of the oleic acids. Skin creams were prepared by using the oleyl oleates as the oily substance and glycerol monooleates and sucrose monooleates which are oleic acid derivatives having the same purities as those of the corresponding oleyl oleates, respectively, as the surfactants according to the formulation described below and the feeling in use was evaluated. The results are shown in Table 9.

| Formulation | |
|---|---|
| oily components | |
| oily substance: oleyl oleate | 40% |
| surfactants: glycerol monooleate | 2.5% |
| sucrose monooleate | 1.5 |
| watery components | |
| purified water | 53% |
| propylene glycol | 3% |

TABLE 9

| | purity of cis-Δ9-octadecenoic acid (%) | purity of cis-Δ9-alkenoic acid (%) | evaluation of feeling in use (number of persons) |
|---|---|---|---|
| Example 41 | 99.9 | 100 | 20 |
| Example 42 | 99 | 99.5 | 19 |
| Example 43 | 95 | 97 | 18 |
| Example 44 | 90 | 93 | 16 |
| Example 45 | 85 | 90 | 13 |
| Comparative Example 25 | 80 | 86 | 8 |

TABLE 9-continued

| | purity of cis-Δ9-octadecenoic acid (%) | purity of cis-Δ9-alkenoic acid (%) | evaluation of feeling in use (number of persons) |
|---|---|---|---|
| Comparative Example 26 | 70 | 78 | 0 |
| Comparative Example 27 | 57 | 66 | 0 |

Examples 46 to 50 and Comparative Examples 28 to 30

Skin creams were prepared by using glycerol trioleates which are oleic acid derivatives having different purities shown in Table 10 as the oily substance and sorbitan sesquioleates and polyoxyethylated (20 mols) sorbitan monooleates which are oleic acid derivatives having the same purities as those of the corresponding glycerol trioleates, respectively, as the surfactants according to the formulation described below and the feeling in use was evaluated. The results are shown in Table 10.

| Formulation | | |
|---|---|---|
| oily components | | |
| oily substance: | glycerol trioleate | 75% |
| surfactants: | sorbitan sesquioleate | 3.5% |
| | polyoxyethylated (20 mols) sorbitan monooleate | 1.5% |
| watery components: | | |
| | purified water | 17% |
| | sorbitol | 3% |

Table 10

| | purity of cis-Δ9-octadecenoic acid (%) | purity of cis-Δ9-alkenoic acid (%) | evaluation of feeling in use (number of persons) |
|---|---|---|---|
| Example 46 | 99.9 | 100 | 19 |
| Example 47 | 99 | 99.5 | 19 |
| Example 48 | 95 | 97 | 18 |
| Example 49 | 90 | 93 | 15 |
| Example 50 | 86 | 90 | 13 |
| Comparative Example 28 | 80 | 86 | 7 |
| Comparative Example 29 | 70 | 78 | 0 |
| Comparative Example 30 | 57 | 66 | 0 |

Examples 51 to 55 and Comparative Examples 31 to 33

Skin creams were prepared by using 2-octyldodecyl oleates which are oleic acid derivatives having different purities shown in Table 11 as the oily substance and pentaerythritol monooleates and polyoxyethylated (20 mols) oleyl ethers which are oleic acid derivatives having the same purities as those of the corresponding 2-octyldodecyl oleates, respectively, as the surfactants according to the formulation described below and the feeling in use was evaluated. The results are shown in Table 11.

shown in Table 13 as the oily substance and L-arginine oleates which are oleic acid derivatives having the same purities as those of the corresponding glycerol dioleates as the surfactant according to the formulation described below and the feeling in use was evaluated. The results are shown in Table 13.

| Formulation | | |
|---|---|---|
| oily components | | |
| oily substance: | 2-octyldodecyl oleate | 20% |
| surfactants: | pentaerythritol monooleate | 2% |
| | polyoxyethylated (20 mols) oleyl ether | 1% |
| watery components | | |
| | purified water | 72% |
| | glycerol | 5% |

TABLE 11

| | purity of cis-Δ9-octa-decenoic acid (%) | purity of cis-Δ9-alkenoic acid (%) | evaluation of feeling in use (number of persons) |
|---|---|---|---|
| Example 51 | 99.9 | 100 | 20 |
| Example 52 | 99 | 99.5 | 19 |
| Example 53 | 95 | 97 | 18 |
| Example 54 | 90 | 93 | 18 |
| Example 55 | 85 | 90 | 14 |
| Comparative Example 31 | 80 | 86 | 9 |
| Comparative Example 32 | 70 | 78 | 7 |
| Comparative Example 33 | 57 | 66 | 0 |

Examples 56 to 60 and Comparative Examples 34 to 36

Milk lotions were prepared by using oleic acids having different purities shown in Table 12 and cholesterol oleates which are derivatives of these oleic acids as the oily substances and L-α-dioleoyl phosphatidyl cholines which are oleic acid derivatives having the same purities as those of the corresponding oleic acids as the surfactant according to the formulation described below and the feeling in use was evaluated. The results are shown in Table 12.

| Formulation | | |
|---|---|---|
| oily components | | |
| oily substances: | oleic acid | 2% |
| | cholesterol oleate | 10 |
| surfactant: | L-α-dioleoyl phosphatidyl choline | 2% |
| watery component | | |
| | purified water | 86% |

TABLE 12

| | purity of cis-Δ9-octa-decenoic acid (%) | purity of cis-Δ9-alkenoic acid (%) | evaluation of feeling in use (number of persons) |
|---|---|---|---|
| Example 56 | 99.9 | 100 | 20 |
| Example 57 | 99 | 99.5 | 19 |
| Example 58 | 95 | 97 | 18 |
| Example 59 | 90 | 93 | 18 |
| Example 60 | 85 | 90 | 15 |
| Comparative Example 34 | 80 | 86 | 10 |
| Comparative Example 35 | 70 | 78 | 7 |
| Comparative Example 36 | 57 | 66 | 0 |

Examples 61 to 65 and Comparative Examples 37 to 39

Milk lotions were prepared by using glycerol dioleates which are oleic acid derivatives having different purities shown in Table 13 as the oily substance and L-arginine oleates which are oleic acid derivatives having the same purities as those of the corresponding glycerol dioleates as the surfactant according to the formulation described below and the feeling in use was evaluated. The results are shown in Table 13.

| Formulation | | |
|---|---|---|
| oily components | | |
| oily substance: | glycerol dioleate | 15% |
| surfactant: | L-arginine oleate | 1% |
| watery component | | |
| | purified water | 84% |

TABLE 13

| | purity of cis-Δ9-octa-decenoic acid (%) | purity of cis-Δ9-alkenoic acid (%) | evaluation of feeling in use (number of persons) |
|---|---|---|---|
| Example 61 | 99.9 | 100 | 20 |
| Example 62 | 99 | 99.5 | 20 |
| Example 63 | 95 | 97 | 18 |
| Example 64 | 90 | 93 | 18 |
| Example 65 | 85 | 90 | 18 |
| Comparative Example 37 | 80 | 86 | 14 |
| Comparative Example 38 | 70 | 78 | 9 |
| Comparative Example 39 | 57 | 66 | 0 |

Examples 66 to 70 and Comparative Examples 40 to 42

Milk lotions were prepared by using tocopherol oleates which are oleic acid derivatives having different purities shown in Table 14 as the oily substance and sucrose monooleates which are oleic acid derivatives having the same purities as those of the corresponding tocopherol oleates as the surfactant according to the formulation described below and the feeling in use was evaluated. The results are shown in Table 14.

| Formulation | | |
|---|---|---|
| oily components | | |
| oily substance: | tocopherol oleate | 10% |
| surfactant: | sucrose monooleate | 3% |
| watery components | | |
| | purified water | 84% |
| | glycerol | 3% |

TABLE 14

| | purity of cis-Δ9-octa-decenoic acid (%) | purity of cis-Δ9-alkenoic acid (%) | evaluation of feeling in use (number of persons) |
|---|---|---|---|
| Example 66 | 99.9 | 100 | 20 |
| Example 67 | 99 | 99.5 | 19 |
| Example 68 | 95 | 97 | 18 |
| Example 69 | 90 | 93 | 15 |
| Example 70 | 85 | 90 | 13 |
| Comparative Example 40 | 80 | 86 | 7 |

TABLE 14-continued

| | purity of cis-Δ9-octa-decenoic acid (%) | purity of cis-Δ9-alkenoic acid (%) | evaluation of feeling in use (number of persons) |
|---|---|---|---|
| Comparative Example 41 | 70 | 78 | 0 |
| Comparative Example 42 | 57 | 66 | 0 |

Examples 71 to 75 and Comparative Examples 43 to 45

Cleansing creams were prepared by using isopropyl oleates which are oleic acid derivatives having different purities shown in Table 15 as the oily substance and polyoxyethylated (20 mols) oleyl ethers and polyoxyethylated (5 mols) sorbitan monooleates which are oleic acid derivatives having the same purities as those of the corresponding isopropyl oleates, respectively, as the surfactants according to the formulation described below and the feeling in use was evaluated. The results are shown in Table 15.

| Formulation | | |
|---|---|---|
| oily components | | |
| oily substance: | isopropyl oleate | 80% |
| surfactants: | polyoxyethylated (20 mols) oleyl ether | 3% |
| | polyoxyethylated (5 mols) sorbitan monooleate | 2% |
| watery component | purified water | 15% |

TABLE 15

| | purity of cis-Δ9-octa-decenoic acid (%) | purity of cis-Δ9-alkenoic acid (%) | evaluation of feeling in use (number of persons) |
|---|---|---|---|
| Example 71 | 99.9 | 100 | 20 |
| Example 72 | 99 | 99.5 | 20 |
| Example 73 | 95 | 97 | 18 |
| Example 74 | 90 | 93 | 18 |
| Example 75 | 85 | 90 | 13 |
| Comparative Example 43 | 80 | 86 | 7 |
| Comparative Example 44 | 70 | 78 | 0 |
| Comparative Example 45 | 57 | 66 | 0 |

Examples 76 to 80 and Comparative Examples 46 to 48

Cleansing foams were prepared by using oleyl alcohols which are oleic acid derivatives having different purities shown in Table 16 as the oily substance and potassium oleates which are oleic acid derivatives having the same purities as those of the corresponding oleyl alcohols as the surfactant according to the formulation described below and the feeling in use was evaluated. The results are shown in Table 16.

| Formulation | | |
|---|---|---|
| oily components | | |
| oily substance: | oleyl alcohol | 3% |
| surfactant: watery component | potassium oleate | 40% |
| | purified water | 57% |

TABLE 16

| | purity of cis-Δ9-octa-decenoic acid (%) | purity of cis-Δ9-alkenoic acid (%) | evaluation of feeling in use (number of persons) |
|---|---|---|---|
| Example 76 | 99.9 | 100 | 20 |
| Example 77 | 99 | 99.5 | 19 |
| Example 78 | 95 | 97 | 18 |
| Example 79 | 90 | 93 | 18 |
| Example 80 | 85 | 90 | 14 |
| Comparative Example 46 | 80 | 86 | 9 |
| Comparative Example 47 | 70 | 78 | 0 |
| Comparative Example 48 | 57 | 66 | 0 |

Examples 81 to 85 and Comparative Examples 49 to 51

Cleansing foams were prepared by using ethylene glycol monooleates which are oleic acid derivatives having different purities shown in Table 17 as the oily substance and monosodium N-oleoylglutamates which are oleic acid derivatives having the same purities as those of the corresponding ethylene glycol monooleates as the surfactant according to the formulation described below and the feeling in use was evaluated. The results are shown in Table 17.

| Formulation | | |
|---|---|---|
| oily components | | |
| oily substance: | ethylene glycol monooleate | 5% |
| surfactant: | monosodium N-oleoylglutamate | 40% |
| watery components | | |
| | purified water | 50% |
| | polyethylene glycol | 5% |

TABLE 17

| | purity of cis-Δ9-octa-decenoic acid (%) | purity of cis-Δ9-alkenoic acid (%) | evaluation of feeling in use (number of persons) |
|---|---|---|---|
| Example 81 | 99.9 | 100 | 20 |
| Example 82 | 99 | 99.5 | 19 |
| Example 83 | 95 | 97 | 18 |
| Example 84 | 90 | 93 | 18 |
| Example 85 | 85 | 90 | 14 |
| Comparative Example 49 | 80 | 86 | 8 |
| Comparative Example 50 | 70 | 78 | 7 |
| Comparative Example 51 | 57 | 66 | 0 |

Examples 86 to 90 and Comparative Examples 52 to 54

Foundations of milk lotion were prepared by using isooctadecanyl oleates which are oleic acid derivatives having different purities shown in Table 18 as the oily substance and triethanolamine oleates which are oleic acid derivatives having the same purities as those of the corresponding isooctadecanyl oleates as the surfactant according to the formulation described below and the feeling in use was evaluated. The results are shown in Table 18.

| Formulation | |
|---|---|
| oily components | |
| oily substance: isooctadecanyl oleate | 18% |
| surfactant: triethanolamine oleate | 5% |
| watery component | |
| purified water | 64.9% |
| pigments | |
| titanium dioxide | 8% |
| talc | 4% |
| color | 0.1% |

TABLE 18

| | purity of cis-Δ9-octadecenoic acid (%) | purity of cis-Δ9-alkenoic acid (%) | evaluation of feeling in use (number of persons) |
|---|---|---|---|
| Example 86 | 99.9 | 100 | 20 |
| Example 87 | 99 | 99.5 | 20 |
| Example 88 | 95 | 97 | 18 |
| Example 89 | 90 | 93 | 18 |
| Example 90 | 85 | 90 | 18 |
| Comparative Example 52 | 80 | 86 | 13 |
| Comparative Example 53 | 70 | 78 | 8 |
| Comparative Example 54 | 57 | 66 | 0 |

Examples 91 to 95 and Comparative Examples 55 to 57

Lipsticks were prepared by using docosenyl oleates and octacosanyl oleates which are oleic acid derivatives having different purities shown in Table 19, respectively, as the oily substances and glycerol monooleates which are oleic acid derivatives having the same purifies as those of the corresponding docosenyl oleates and octacosanyl oleates as the surfactant according to the formulation described below and the feeling in use was evaluated. The results are shown in Table 19.

| Formulation | |
|---|---|
| oily components | |
| oily substances: docosenyl oleate | 42% |
| octacosanyl oleate | 15% |
| surfactant: glycerol monooleate | 30% |
| watery component | |
| glycerol | 3% |
| pigments | |
| titanium dioxide | 1% |
| red pigment No. 201 | 1% |
| red pigment No. 202 | 1% |
| blue pigment No. 1 auminum chelate | 0.5% |
| mica titanium | 6.5% |

TABLE 19

| | purity of cis-Δ9-octadecenoic acid (%) | purity of cis-Δ9-alkenoic acid (%) | evaluation of feeling in use (number of persons) |
|---|---|---|---|
| Example 91 | 99.9 | 100 | 20 |
| Example 92 | 99 | 99.5 | 19 |
| Example 93 | 95 | 97 | 18 |
| Example 94 | 90 | 93 | 18 |
| Example 95 | 85 | 90 | 14 |
| Comparative Example 55 | 80 | 86 | 9 |
| Comparative Example 56 | 70 | 78 | 7 |
| Comparative Example 57 | 57 | 66 | 0 |

Examples 96 to 100 and Comparative Examples 58 to 60

Hair creams were prepared by using octadecyl oleates which are oleic acid derivatives having different purities shown in Table 20 as the oily substance and polyoxyethylene (10 mols) glycol monooleates which are oleic acid derivatives having the same purities as those of the corresponding octadecyl oleates as the surfactant according to the formulation described below and the feeling in use was evaluated. The results are shown in Table 20.

| Formulation | |
|---|---|
| oily components | |
| oily substance: octadecyl oleate | 15% |
| surfactant: polyoxylethylene (10 mols) glycol monooleate | 5% |
| watery components | |
| purified water | 75% |
| propylene glycol | 5% |

TABLE 20

| | purity of cis-Δ9-octadecenoic acid (%) | purity of cis-Δ9-alkenoic acid (%) | evaluation of feeling in use (number of persons) |
|---|---|---|---|
| Example 96 | 99.9 | 100 | 20 |
| Example 97 | 99 | 99.5 | 19 |
| Example 98 | 95 | 97 | 18 |
| Example 99 | 90 | 93 | 18 |
| Example 100 | 85 | 90 | 13 |
| Comparative Example 58 | 80 | 86 | 8 |
| Comparative Example 59 | 70 | 78 | 0 |
| Comparative Example 60 | 57 | 66 | 0 |

Examples 101 to 105 and Comparative Examples 61 to 63

Hair growth agents were prepared by using ethyl oleates which are oleic acid derivatives having different purifies shown in Table 21 as the oily substance and glycerol monooleates which are oleic acid derivatives having the same purifies as those of the corresponding ethyl oleates as the surfactant according to the formulation described below and the feeling in use was evaluated. The results are shown in Table 21.

| Formulation | |
|---|---|
| oily components | |
| oily substance: ethyl oleate | 3% |
| surfactant: glycerol monooleate | 2% |
| watery component | |
| ethanol | 93.4% |
| hair growth components | |
| cepharanthin | 1% |
| hinokitiol | 0.1% |
| tocopherol nicotinate | 0.5% |

TABLE 21

| | purity of cis-Δ9-octadecenoic acid (%) | purity of cis-Δ9-alkenoic acid (%) | evaluation of feeling in use (number of persons) |
|---|---|---|---|
| Example 101 | 99.9 | 100 | 20 |
| Example 102 | 99 | 99.5 | 20 |
| Example 103 | 95 | 97 | 19 |
| Example 104 | 90 | 93 | 18 |
| Example 105 | 85 | 90 | 14 |
| Comparative Example 61 | 80 | 86 | 7 |
| Comparative Example 62 | 70 | 78 | 1 |
| Comparative Example 63 | 57 | 66 | 0 |

Examples 106 to 110 and Comparative Examples 64 to 66

Hair growth agents were prepared by using palmityl oleates which are oleic acid derivatives having different purities shown in Table 22 as the oily substance and polyoxyethylene (10 mols) oleyl ether phosphoric acid sodium salts which are oleic acid derivatives having the same purities as those of the corresponding palmityl oleates as the surfactants according to the formulation described below and the feeling in use was evaluated. The results are shown in Table 22.

| Formulation | |
|---|---|
| oily components | |
| oily substance: palmityl oleate | 2% |
| surfactants: polyoxyethylene (10 mols) oleyl ether phosphoric acid sodium salt | 2% |
| watery components | |
| ethanol | 70% |
| purified water | 24.4% |
| hair growth components | |
| capronium chloride | 1% |
| extract of Japanese green gentian | 0.1% |
| α-tocopherol | 0.5% |

TABLE 22

| | purity of cis-Δ9-octadecenoic acid (%) | purity of cis-Δ9-alkenoic acid (%) | evaluation of feeling in use (number of persons) |
|---|---|---|---|
| Example 106 | 99.9 | 100 | 20 |
| Example 107 | 99 | 99.5 | 19 |

TABLE 22-continued

| | purity of cis-Δ9-octadecenoic acid (%) | purity of cis-Δ9-alkenoic acid (%) | evaluation of feeling in use (number of persons) |
|---|---|---|---|
| Example 108 | 95 | 97 | 18 |
| Example 109 | 90 | 93 | 18 |
| Example 110 | 85 | 90 | 13 |
| Comparative Example 64 | 80 | 86 | 9 |
| Comparative Example 65 | 70 | 78 | 0 |
| Comparative Example 66 | 57 | 66 | 0 |

Examples 111 to 115 and Comparative Examples 67 to 69

Emulsion compositions were prepared by using glycerol trioleates which are oleic acid derivatives having different purities shown in Table 23 as the oily substance and sorbitan sesquioleates and polyoxyethylene (20 mols) sorbitan monooleates which are oleic acid derivatives having the same purities as those of the corresponding glycerol trioleates, respectively, as the surfactants according to the formulation described below.

| Formulation | |
|---|---|
| oily components | |
| oily substance: glycerol trioleate | 50% |
| surfactants: sorbitan sesquioleate | 8.5% |
| polyoxylethylene (20 mols) sorbitan monooleate | 1.5 |
| watery component | |
| purified water | 40% |

TABLE 23

| | purity of cis-Δ9-octadecenoic acid (%) | purity of cis-Δ9-alkenoic acid (%) |
|---|---|---|
| Example 111 | 99.9 | 100 |
| Example 112 | 99 | 99.5 |
| Example 113 | 95 | 97 |
| Example 114 | 90 | 93 |
| Example 115 | 85 | 90 |
| Comparative Example 67 | 80 | 86 |
| Comparative Example 68 | 70 | 78 |
| Comparative Example 69 | 57 | 66 |

Storage stability of the emulsion compositions thus prepared was evaluated. The results on the condition of the emulsion and the storage stability on standing are shown in Table 24.

TABLE 24

| | condition of emulsion | storage stability on standing, after the specified time | | | | |
|---|---|---|---|---|---|---|
| | | 30 min. | 1 hour | 5 hours | 24 hours | 72 hours |
| Example 111 | good | stable | stable | stable | stable | stable |
| Example 112 | good | stable | stable | stable | stable | stable |
| Example 113 | good | stable | stable | stable | stable | stable |
| Example 114 | good | stable | stable | stable | stable | stable |
| Example 115 | good | stable | stable | stable | stable | slightly separated |
| Comparative Example 67 | good | stable | stable | slighly separated | separated | separated |
| Comparative Example 68 | good | stable | slighly separated | separated | separated | separated |
| Comparative Example 69 | good | stable | slightly separated | separated | separated | separated |

Comparative Examples 70 to 72

Emulsion compositions were prepared by the same method used in Examples 111 to 115 and in Comparative Examples 67 to 69 except that sorbitan sesquioleate and polyoxyethylene (20 mols) sorbitan monooleate as the surfactants were replaced by 8.5% of sorbitan sesquistearate which is a derivative of 99% stearic acid and 1.5% of polyoxyethylene (20 mols) sorbitan monostearate as the surfactants in Comparative Example 70, by 10% of polyoxyethylene (2 mols) nonylphenyl ether as the surfactant in Comparative Example 71 and by 10% of glycerol monolaurate which is a derivative of 99% lauric acid as the surfactant in Comparative Example 72 and the storage stability of emulsion was evaluated. The results are shown in Table 25. The results show that the storage stability of emulsion is inferior when the compounds other than the derivatives of cis-Δ9-octadecenoic acid are used as the surfactant.

TABLE 25

| | condition of emulsion | storage stability on standing, after the specified time | | | |
|---|---|---|---|---|---|
| | | 30 min. | 1 hour | 5 hours | 24 hours |
| Comparative Example 70 | poor | separated | separated | separated | separated |
| Comparative Example 71 | poor | slightly separated | slightly separated | separated | separated |
| Comparative Example 72 | poor | slightly separated | separated | separated | separated |

Examples 116 to 120 and Comparative Examples 73 to 75

Emulsion compositions were prepared by using ethyl oleates which are oleic acid derivatives having different purities shown in Table 26 as the oily substance and sorbitan sesquioleates and polyoxyethylene (20 mols) sorbitan monooleates which are oleic acid derivatives having the same purities as those of the corresponding ethyl oleates, respectively, as the surfactants according to the formulation described below.

| Formulation | |
|---|---|
| oily components | |
| oily substance: ethyl oleate | 50% |
| surfactants: sorbitan sesquioleate | 7.5% |
| polyoxylethylene (20 mols) sorbitan monooleate | 2.5% |
| watery component | |
| purified water | 40% |

TABLE 26

| | purity of cis-Δ9-octadecenoic acid (%) | purity of cis-Δ9-alkenoic acid (%) |
|---|---|---|
| Example 116 | 99.9 | 100 |
| Example 117 | 99 | 99.5 |
| Example 118 | 95 | 97 |
| Example 119 | 90 | 93 |
| Example 120 | 85 | 90 |
| Comparative Example 73 | 80 | 86 |
| Comparative Example 74 | 70 | 78 |
| Comparative Example 75 | 57 | 66 |

Storage stability of the emulsion compositions thus prepared was evaluated. The results on the condition of the emulsion and the storage stability on standing are shown in Table 27.

TABLE 27

| | condition of emulsion | storage stability on standing, after the specified time | | | | |
|---|---|---|---|---|---|---|
| | | 30 min. | 1 hour | 5 hours | 24 hours | 72 hours |
| Example 116 | good | stable | stable | stable | stable | stable |
| Example 117 | good | stable | stable | stable | stable | stable |
| Example 118 | good | stable | stable | stable | stable | stable |
| Example 119 | good | stable | stable | stable | stable | slightly separated |
| Example 120 | good | stable | stable | stable | stable | slightly separated |
| Comparative Example 73 | good | stable | stable | slightly separated | separated | separated |
| Comparative Example 74 | good | stable | slightly separated | separated | separated | separated |
| Comparative | good | stable | slightly | sep- | sep- | sep- |

TABLE 27-continued

| condition of emulsion | storage stability on standing, after the specified time | | | | |
|---|---|---|---|---|---|
| | 30 min. | 1 hour | 5 hours | 24 hours | 72 hours |
| Example 75 | | | separated | arated | arated | arated |

Examples 121 to 125 and Comparative Examples 76 to 78

Emulsion compositions were prepared by using oleyl alcohols which are oleic acid derivatives having different purities shown in Table 28 as the oily substance and sorbitan sesquioleates and polyoxyethylene (20 mols) sorbitan monooleates which are oleic acid derivatives having the same purities as those of the corresponding oleyl alcohols, respectively, as the surfactants according to the formulation described below.

| Formulation | |
|---|---|
| oily components | |
| oily substance: oleyl alcohol | 50% |
| surfactants: sorbitan sesquioleate | 8.5% |
| polyoxylethylene (20 mols) sorbitan monooleate | 1.5 |
| watery component | |
| purified water | 40% |

TABLE 28

| | purity of cis-Δ9-octadecenoic acid (%) | purity of cis-Δ9-alkenoic acid (%) |
|---|---|---|
| Example 121 | 99.9 | 100 |
| Example 122 | 99 | 99.5 |
| Example 123 | 95 | 97 |
| Example 124 | 90 | 93 |
| Example 125 | 85 | 90 |
| Comparative Example 76 | 80 | 86 |
| Comparative Example 77 | 70 | 78 |
| Comparative Example 78 | 57 | 66 |

Storage stability of the emulsion compositions thus prepared was evaluated. The results on the condition of the emulsion and the storage stability on standing are shown in Table 29.

TABLE 29

| | condition of emulsion | storage stability on standing, after the specified time | | | | |
|---|---|---|---|---|---|---|
| | | 30 min. | 1 hour | 5 hours | 24 hours | 72 hours |
| Example 121 | good | stable | stable | stable | stable | stable |
| Example 122 | good | stable | stable | stable | stable | stable |
| Example 123 | good | stable | stable | stable | stable | stable |
| Example 124 | good | stable | stable | stable | stable | stable |
| Example 125 | good | stable | stable | stable | stable | stable |
| Comparative Example 76 | good | stable | stable | stable | stable | separated |
| Comparative Example 77 | good | stable | stable | stable | separated | separated |
| Comparative Example 78 | good | stable | stable | slightly separated | separated | separated |

As the results in Tables 24, 25, 27 and 29 show, the emulsion compositions having very excellent storage stability can be prepared by the formulations of Examples 111 to 125, which contain oleic acid or oleic acid derivatives containing cis-Δ-9-octadecenoic acid in high concentrations as the oily substance and oleic acid derivatives containing cis-Δ9-octadecenoic acid in high concentrations as the surfactant.

INDUSTRIAL APPLICABILITY

As described above, the cosmetic composition of the invention is useful as various kinds of cosmetic materials, such as skin lotion, cream, milk lotion, cleansing foam and the like.

The emulsion composition of the invention can provide an emulsion having excellent storage stability of emulsion. This emulsion can be utilized as a base material for pharmaceuticals, an emulsifying agent for oily materials which are not easily emulsified and the like as well as the cosmetic material.

We claim:

1. An emulsion composition which comprises 0.1 to 99 weight % of a first component and 99.9 to 1 weight % of a second component which is water soluble, the first component comprising 85 or more weight % of a cis-Δ9-octadecenoic acid or a derivative thereof, included within 90 weight % or more of a cis-Δ9-alkenoic acid or a derivative thereof, wherein the first component is either insoluble in the second component, dissolved in the second component or emulsified in the second component.

2. An emulsion composition as claimed in claim 1, wherein the first component comprises a mixture of a substance insoluble in the second component and a surfactant dissolved or emulsified in the second component.

3. An emulsion composition as claimed in claim 2, wherein the substance insoluble in the second component is an ester or a monohydric alcohol.

4. An emulsion composition as claimed in claim 2, wherein the ester insoluble in the second component is an ester of cis-Δ9-octadecenoic acid and a monohydric alcohol or an ester of cis-Δ9-octadecenoic acid and a polyhydric alcohol.

5. An emulsion composition as claimed in claim 2, wherein the monohydric alcohol insoluble in the second component is cis-Δ9-octadecenol.

6. An emulsion composition as claimed in claim 2, wherein the surfactant dissolved or emulsified in the second component is an ester of cis-Δ9-octadecenoic acid and a polyhydric alcohol or an ester of cis-Δ9-octadecenoic acid and a polyoxyethylated polyhydric alcohol.

7. An emulsion composition as claimed in claim 1, wherein the second component is water, an alcohol, a sugar, a mucopolysaccharide, an amino acid or a protein.

8. The emulsion composition of claim 1, wherein the first component contains fatty acids other than cis-Δ9-alkenoic acid, or derivatives of fatty acids other than cis-Δ9-alkenoic acids or mixtures thereof.

9. The emulsion composition of claim 1, wherein the first component comprises derivatives of the cis-Δ9-alkenoic acids, including cis-Δ9-octadecenoic acid, are salts of the acids, amides of the acids, esters of the acids, cis-Δ9-alkenols, ethers of cis-Δ9-alkenols, esters of cis-Δ9-alkenols, cis-Δ9-alkenylamines, salts of cis-Δ9-alkenylamines with an acid or quaternary ammonium salts of cis-Δ9-alkenylamines.

10. The emulsion composition of claim 1, wherein the first component comprises derivatives of the cis-Δ9-alkenoic acids, including cis-Δ9-octadecenoic acid, selected from the group consisting of: salts of the acids with alkali metals, alkylamines, alkanolamines or basic amino acids; ammonium salts of the acids; morpholine salts of the acids; amides of the acids with alkylamines, alkenylamines, alkanolamines, amino acids or N-methyltaurine; polyoxyethylated or polyoxypropylated compounds of amides of the acids with alkylamines, alkenylamines or alkanolamines; cis-Δ9-alkenoyl peptides; esters of the acids with monohydric alcohols or polyoxyethylated or polyoxypropylated compounds of monohydric alcohols; esters of the acids with polyhydric alcohols or polyoxyethylated or polyoxypropylated compounds of polyhydric alcohols; esters of the acids with sugar compounds; esters and salts of the acids with sterols; esters of the acids with tocopherol, oryzanol, guaiacol, gossypol, terpene alcohols, fluoroalcohols, or isethionic acid; phospholipids wherein the acyl group of a cis-Δ9-alkenoic acid is introduced; cis-Δ9-alkenols and polyoxyethylated or polyoxypropylated compounds thereof; phosphoric esters, sulfuric esters, polyoxyethylated phosphoric esters, polyoxyethylated sulfuric esters, polyoxypropylated phosphoric esters, or polyoxypropylated sulfuric esters of cis-Δ9-alkenols and salts thereof; esters, partial esters or partial ester salts of cis-Δ9-alkenyl alcohols with carboxylic acids or hydroxylated carboxylic acids; ethers of cis-Δ9-alkenols with alcohols, or sugars of other hydroxyl compounds; salts of cis-Δ9-alkenylamines with acids; quaternary ammonium salts having a cis-Δ9-alkenyl group; and, quaternary ammonium betaine having a cis-Δ9-alkenyl group.

11. The emulsion composition of claim 1, wherein the first component comprises derivatives of the cis-Δ9-alkenoic acids, including cis-Δ9-octadecenoic acid, selected from the group consisting of: esters of cis-Δ9-octadecenoic acid with ethanol, isopropanol, cis-Δ9-hexadecanol, cis-Δ9-octadecanol, isooctadecanol, cholesterol and tocopherol; glycerol tri-cis-Δ9-octadecenoate; and, cis-Δ9-octadecenol.

12. The emulsion composition of claim 1, wherein the first component contains: fatty acids other than cis-Δ9-alkenoic acid; derivatives of fatty acids other than cis-Δ9-alkenoic acids; paraffin; kerosene; squalene; plant oils; animal oils; lanoline; haze wax; hexadecanol; isooctadecanol; silicone oils; fluorohydrocarbons; polyoxypropylated ethers; cholesterol; tocopherol; dodecandiethanolamide; or a polyoxyethylated alkylphenyl ether.

* * * * *